United States Patent
Shan et al.

(10) Patent No.: US 11,419,575 B2
(45) Date of Patent: Aug. 23, 2022

(54) APPARATUS FOR VISUALIZING TISSUE PROPERTY

(71) Applicant: KONINKLIJKE PHILIPS N.V., Eindhoven (NL)

(72) Inventors: Caifeng Shan, Veldhoven (NL); Godefridus Antonius Harks, Ruen (NL); Harm Jan Willem Belt, Weert (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 552 days.

(21) Appl. No.: 15/525,605

(22) PCT Filed: Nov. 11, 2015

(86) PCT No.: PCT/EP2015/076366
§ 371 (c)(1),
(2) Date: May 10, 2017

(87) PCT Pub. No.: WO2016/078992
PCT Pub. Date: May 26, 2016

(65) Prior Publication Data
US 2017/0332997 A1 Nov. 23, 2017

(30) Foreign Application Priority Data
Nov. 18, 2014 (EP) .................................. 14193734

(51) Int. Cl.
*A61B 8/08* (2006.01)
*G01S 7/52* (2006.01)
(Continued)

(52) U.S. Cl.
CPC ............ *A61B 8/0883* (2013.01); *A61B 8/469* (2013.01); *A61B 8/486* (2013.01); *A61B 8/5223* (2013.01);
(Continued)

(58) Field of Classification Search
CPC ....... A61B 8/0883; A61B 8/469; A61B 8/486; A61B 8/5223; A61B 18/18; A61B 2017/00044; G01S 7/52042
See application file for complete search history.

(56) References Cited

U.S. PATENT DOCUMENTS 5,820,561 A  10/1998 Olstad et al.
7,881,790 B1 *  2/2011 Turcott .............. A61B 5/14551
607/17

(Continued)

FOREIGN PATENT DOCUMENTS

JP  2007125273 A  5/2007
WO  2011046879  4/2011

OTHER PUBLICATIONS

Dendel et al., Strain and Strain Rate Imaging by Echocardiography—Basic Concepts and Clinical Applicability, Current Cardiology Reviews, 2009, 5, 133-148) (Year: 2009).*

(Continued)

*Primary Examiner* — Amelie R Davis
*Assistant Examiner* — John Denny Li

(57) ABSTRACT

The present invention relates to an apparatus (1) comprising a signal processor (2) for processing measurement signals (3) from a motion-mode ultrasound measurement and a rendering device (4) coupled to a processor (2) for rendering a one-dimensional representation (40) along a temporal axis (41) indicative of a property within a tissue. The values (42) in the one-dimensional representation (40) are derived on the basis of measured values in an observation window (12, 22, 32) defined on an M-mode ultrasound image (10), a tissue velocity image (20) or a strain rate image (30).

19 Claims, 13 Drawing Sheets

(51) Int. Cl.
  *A61B 8/00* (2006.01)
  *A61N 7/00* (2006.01)
  *A61B 18/18* (2006.01)
  *A61B 17/00* (2006.01)
  *A61B 90/00* (2016.01)
  *A61B 8/12* (2006.01)
  *A61B 18/12* (2006.01)
  *A61B 18/20* (2006.01)

(52) U.S. Cl.
  CPC ............... *A61B 8/543* (2013.01); *A61N 7/00* (2013.01); *G01S 7/52042* (2013.01); *G01S 7/52066* (2013.01); *G01S 7/52074* (2013.01); *A61B 8/12* (2013.01); *A61B 8/463* (2013.01); *A61B 8/485* (2013.01); *A61B 18/12* (2013.01); *A61B 18/18* (2013.01); *A61B 18/20* (2013.01); *A61B 2017/00044* (2013.01); *A61B 2090/364* (2016.02); *A61B 2090/378* (2016.02)

(56) References Cited

U.S. PATENT DOCUMENTS

| | | | |
|---|---|---|---|
| 2002/0040187 A1* | 4/2002 | Alam | A61B 5/0053 600/442 |
| 2003/0149365 A1* | 8/2003 | Torp | A61B 8/485 600/450 |
| 2004/0111028 A1 | 6/2004 | Abe et al. | |
| 2005/0096543 A1 | 5/2005 | Jackson et al. | |
| 2006/0281993 A1* | 12/2006 | Pedrizzetti | A61B 8/0858 600/443 |
| 2009/0105588 A1 | 4/2009 | Emelianov et al. | |
| 2009/0143676 A1 | 6/2009 | Matsumura | |
| 2012/0128223 A1 | 5/2012 | Rivaz et al. | |
| 2013/0046178 A1 | 2/2013 | Cho et al. | |
| 2013/0066584 A1 | 3/2013 | Lan et al. | |
| 2013/0204134 A1* | 8/2013 | Harks | A61B 5/0084 600/439 |
| 2013/0296743 A1* | 11/2013 | Lee | A61B 8/5223 601/3 |
| 2013/0303880 A1 | 11/2013 | Hsu | |
| 2014/0081144 A1 | 3/2014 | Moehring et al. | |
| 2014/0155750 A1 | 6/2014 | Kim et al. | |
| 2015/0038842 A1 | 2/2015 | Belt et al. | |
| 2015/0204556 A1* | 7/2015 | Kusukame | F24F 11/30 165/237 |
| 2015/0265241 A1 | 9/2015 | Belt | |

OTHER PUBLICATIONS

Kanai, H et al., "Noninvasive evaluation of local myocardial thickening and its color-coded imaging", IEEE Transactions on Ultrasonics, Ferroelectrics and Frequency Control, IEEE, US, vol. 44, No. 4, Jul. 1, 2997, pp. 752-768.

Xia, J. et al., "Considering Angle Selection When Using Ultrasound Electrode Displacement Elastography to Evaluate Radiofrequency Ablation of Tissues". Hindawi Publishing Corporation, BioMed Research International, vol. 2014, Article ID 764320, 11 pages.

* cited by examiner

APPARATUS FOR VISUALIZING TISSUE PROPERTY

CROSS-REFERENCE TO PRIOR APPLICATIONS

This application is the U.S. National Phase application under 35 U.S.C. § 371 of International Application Serial No. PCT/EP2015/076366, filed on Nov. 11, 2015, which claims the benefit of European Patent Application No. 14193734.2, filed on Nov. 18, 2014. These applications are hereby incorporated by reference herein.

FIELD OF THE INVENTION

The invention relates to an apparatus for processing ultrasound measurement signals originated from a tissue exposed to ultrasound waves and a rendering device coupled to the processor for rendering a representation derived from the processed ultrasound measurement signals. The invention further relates to a system delivering energy to the tissue during ultrasound measurement and the apparatus for processing the ultrasound measurement signals.

BACKGROUND OF THE INVENTION

US 2009/0105588 A1 discloses an apparatus, method and system for monitoring and controlling radiotherapy. The radiative source emits energy into a tissue which is absorbed at a target site, to heat the tissue. An ultrasound transducer transmits ultrasound signal to the tissue and receives the reflected ultrasound signal. A signal processor processes the received ultrasound signals and calculates the tissue composition scan or tissue temperature. Ultrasound image, tissue temperature scan and strain image are rendered to determine and/or modify the therapeutic radiative dose based on tissue temperature scan or tissue composition scan. The brightness of the ultrasound image represents the amplitude of scattered and reflected signal from the imaged structures. Color bars indicating the range of temperature change and strain differences are supporting the interpretation of the displayed images.

US2013/0204134 A1 discloses a property determination apparatus for determining a property of an object based on optical sensing data and ultrasound sensing data acquired by an optical sensor and an ultrasound sensor. Light and ultrasound have different penetration depth and scattering in the object. When energy is applied to living tissue, the perfusion of tissue with blood changes, resulting in change of the scattering values determined by the property determination unit for sample windows corresponding to different depths and different times. Alternative optical techniques disclosed for determination of the property of the object are optical spectra and laser doppler flowmetry, whereas for ultrasound based property determination the cross correlation and ultrasound signal reflection are revealed.

SUMMARY OF THE INVENTION

It is an object of the present invention to provide a system with improved efficiency of energy application to a tissue.

According to the invention this object is realized by a system comprising an energy source connected to an energy application device for applying energy to a tissue so as to change the property of the tissue, an ultrasound measurement arrangement and an apparatus, wherein the system is arranged to discontinue transmission of energy from the energy source to the energy application device in response to a detected change of the mean and the variation of strain rate values derived from ultrasound measurement.

The discontinuation of energy application based on a detected change of a physical quantity represents an improvement in efficiency of the energy application to the tissue by avoiding application of energy for an excessive duration.

In an embodiment of the system, the discontinuation of energy transmission to the energy application device is in response to a detected change in the range of 10 to 30 percent. A detected change of the mean and the variation of strain rate values in the range of 10 to 30 percent represents a significant change in tissue contractility, elasticity and perfusion.

In another embodiment of the system, the apparatus comprises a signal processor for processing motion-mode ultrasound measurement signals originated from a tissue exposed to ultrasound waves and a rendering device coupled to the processor for rendering a one-dimensional representation along a temporal axis, with values in the representation indicative of strain rate within the tissue derived on the basis of measured values in a selectable observation window, wherein the observation window is defined by a distance range in spatial direction within the tissue and a time interval in temporal direction, wherein the selection of the observation window is based on a motion-mode ultrasound image, a tissue velocity image, or a strain rate image, wherein the apparatus is arranged to shift the observation window along the temporal axis.

A motion-mode (M-mode) ultrasound measurement is indicating the variation in time of the scattering and the reflection of ultrasound waves along the propagation direction of the ultrasound beam. The brightness of the M-mode ultrasound image represents the amplitude of scattered and reflected signal from the imaged structures received by the ultrasound measurement arrangement. By selecting the observation window on an M-mode ultrasound image, or alternatively on a tissue velocity image or a strain rate image, the focus of processing the measurement signals according to the invention is defined by a distance range in the spatial direction and a time interval in the temporal direction. The apparatus is operable to shift the observation window along the temporal axis, which allows deriving multiple values in time represented along the temporal axis of the one-dimensional representation. Due to shifting the observation window along the temporal axis, the one-dimensional representation presents the recent value in real-time added to the previously derived values. Since the human eyes can compare more easily one-dimensional values along a time span than to detect brightness differences in two-dimensional images over the same time span, the improved presentation of a property of the tissue is readily absorbable by a person.

In an embodiment, the apparatus is operable to visualize motion of a heart of living being. The heart of a living being presents intrinsic electrical activity, which is triggering contraction and relaxation of the heart tissue. The M-mode ultrasound measurement signals are capturing this mechanical activity, and the one-dimensional representation of the derived values resembles the representation of an electrocardiogram of the heart. In yet another embodiment of the system the time interval defining the observation window in the temporal direction is shorter than the time interval between two consecutive heartbeats of the heart of the living being. The refinement of the one-dimensional representation of the mechanical activity of the heart improves such that its progress follows the electrical activity of the heart.

The values in the one-dimensional representation are preferably representing strain rate. Modifications of strain rate values reflect a change in the property of the myocardium upon internal or external factors (eg. myocardial infarct, energy application to tissue), resulting in changes of tissue contractility, elasticity and perfusion. In an embodiment, the system further comprises a measurement unit for measuring an electrical activity of the heart. The apparatus is configured to synchronize the representation of the values in the one-dimensional representation with an electrogram or an electrocardiogram of the heart. Such embodiment enables a person performing the ultrasound measurement to readily absorb the information regarding the mechanical activity of the heart corresponding to its electrical activity. The electrogram may be an electrogram measured locally in the vicinity of the heart, or a surface electrocardiogram measured on a surface of the body of the living being. The electrogram measured locally in the vicinity of the heart may be performed by a device provided with a sensor for sensing electrical activity, the device having the ability to access the internal or external surface of the heart tissue.

In an embodiment of the system according to the invention, the spatial direction of the motion-mode ultrasound measurement comprises a plurality of observation windows, wherein the rendering device coupled to the processor is arranged to render a one-dimensional representation along the temporal axis for each of the plurality of observation windows. Dividing the spatial direction into multiple observation windows results in a refinement of the values in the one-dimensional representations. Moreover, a tissue such as myocardium may present several layers which are reacting differently to internal or external stimuli. The multiple one-dimensional representations originating from the plurality of observation windows improves the visualization of atypical reaction of particular layers of the tissue to various stimuli.

In a further embodiment according to the invention, the rendering device of the apparatus coupled to the processor is operable to render a composite image consisting of a plurality of one-dimensional representations along the temporal axis, wherein the position of each one-dimensional representation in the composite image is according to the subsequent position of the observation windows in the strain rate image, motion-mode ultrasound image or tissue velocity image from which they originate. The composite image consisting of the plurality of one-dimensional representations improves the presentation of the tissue property change upon internal or external stimuli such that a propagation of a property change along the spatial dimension is reflected in the propagation of the change in the values of the subsequent one-dimensional representations. An example of the propagation of property change in the tissue along the spatial dimension is the ablation of tissue with radiofrequency current, where the heating of the tissue results in changes of tissue contractility, elasticity and perfusion.

In an embodiment of the system, an ultrasound transducer of the ultrasound measurement arrangement is integrated into the distal tip of the energy application device. The main advantage of such a system is that the ultrasound probe comprising one or multiple ultrasound transducers can be embedded into the energy application device. This allows localized ultrasound measurement exactly on the site where the energy application to the tissue occurs. Due to the integration of the ultrasound transducers into the energy application device, there is no need for alignment of the ultrasound probe and the energy application device in order to avoid shadowing caused by the energy application device in the ultrasound measurement. Furthermore, the system comprising a measurement unit for measuring electrical activity of the heart allows internal synchronization of the electrograms with the M-mode ultrasound measurement signals. The electrical signal measurement electrodes can be integrated into the distal tip of the energy application device, therefore the system can provide electrograms synchronized with the one-dimensional representation of the mechanical activity of the heart tissue originating from the same location where the energy application to the tissue occurs.

The energy application device is arranged to apply energy to the tissue by one of the modalities selected from ultrasound waves, radiofrequency current, radiofrequency waves, microwaves, or laser radiation. The energy source transmits energy to the energy application device in the form of electrical current or electromagnetic radiation. In the energy application device the electrical current can be transformed in ultrasound waves, or in electromagnetic waves in the form of radio frequency waves, microwaves or light.

This and other aspects of the invention will be apparent from and elucidated with reference to the embodiments described hereinafter.

DETAILED DESCRIPTION OF EMBODIMENTS

Figure 1:
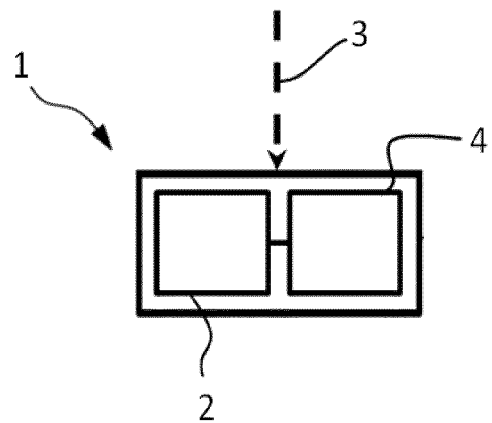
FIG. 1 shows schematically and exemplarily an embodiment of the apparatus according to the invention.

FIG. 1 shows schematically and exemplarily an embodiment of an apparatus 1 comprising a signal processor 2 for processing motion-mode ultrasound measurement signals 3 from a tissue, and a rendering device 4 coupled to the processor 2 for rendering a one-dimensional representation along a temporal axis.

The ultrasound measurement signals 3 are preferably originating from a real-time M-mode pulse/echo measurement on a tissue. Alternatively, the M-mode ultrasound information can be extracted by the signal processor 2 from a brightness-mode (B-mode) or a three-dimensional (3D) ultrasound measurement provided by an external ultrasound measurement apparatus.

The rendering device 4 comprises a rendering processor, a memory unit and a display unit. The rendering processor is arranged to prepare the data received from the processor 2 for being rendered as a one-dimensional representation on the display unit.

The values in the one-dimensional representation are indicative of a property within the tissue. They are derived on the basis of the M-mode ultrasound measurement signal values situated in an observation window within a two-dimensional M-mode representation of the tissue.

Figure 2:
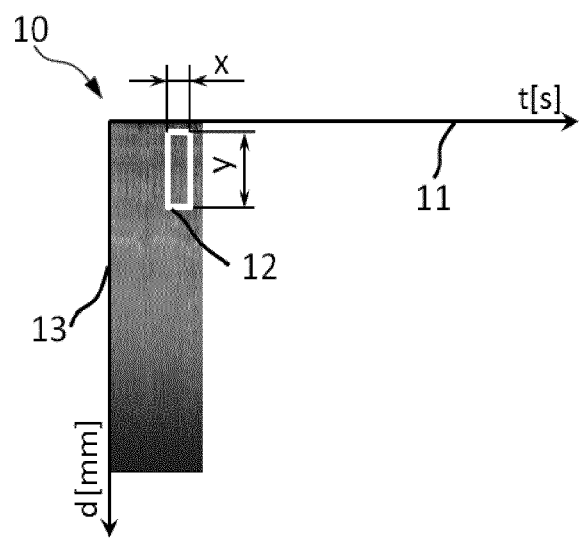
FIG. 2 shows schematically and exemplarily an embodiment for the definition of an observation window.

FIG. 2 shows schematically and exemplarily an image for illustrating a definition of an observation window 12 on an M-mode ultrasound image 10 of heart tissue of a living being. The observation window 12 is defined by a distance y in spatial direction 13 and a time interval x in temporal direction 11. The spatial direction 13 represents the depth of the anatomy, hence the depth of the tissue from which the ultrasound reflections and ultrasound scattering originate upon exposing the anatomy to ultrasound waves. Alternatively, the spatial direction may be expressed in time of flight of the ultrasound waves, which is the time that it takes for ultrasound waves to travel a distance through the tissue.

A program controlled processor and a computer program for the processor is enabling the selection of the observation window based on an M-mode ultrasound image either by selecting the observation window on the M-mode ultrasound image with a pointing device or by indicating the size, coordinate position and the shape of the observation window. The processor arranged for selecting the observation window may be the same processor as the signal processor 2 for processing motion-mode ultrasound measurement signals 3 from the tissue.

Figure 3:
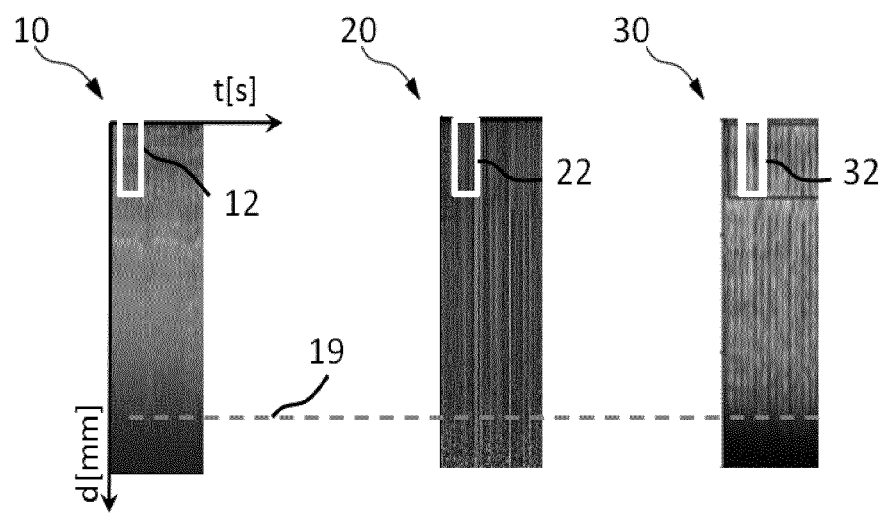
FIG. 3 shows schematically and exemplarily alternative embodiments for the definition of an observation window.

The observation window 12 defined on the M-mode ultrasound image may alternatively be defined on a tissue velocity image 20 or on a strain rate image 30, as exemplarily shown in FIG. 3. When the heart of a living being is the subject of the ultrasound measurement, the ultrasound measurement signals may contain information on multiple anatomical entities such as myocardium, blood, epicardial fat, pericardial liquid, lung, esophagus. The tissue velocity image and the strain rate image derived from the M-mode ultrasound signal show sharper boundaries at the interface between different anatomical entities than the M-mode ultrasound image. A prominent difference between blood and myocardium, between lung and myocardium or between two layers of tissue with dissimilar motion triggered by delayed electrical activity of the respective two layers are such examples where the selection of the observation window from a tissue velocity image or a strain rate image is advantageous.

The tissue velocity image for the selection of the observation window can be rendered based on processing M-mode ultrasound signals by the processor according to $$v = \frac{\Phi}{\pi} \cdot \frac{c \cdot f_p}{4 \cdot f_c} \quad \text{(Eq. 1)}$$

with $\Phi$ the local phase shift between two consecutive radiofrequency lines from the M-mode ultrasound measurement, c the speed of sound in the tissue, $f_p$ the pulse repetition rate of the ultrasound measurement and $f_c$ the center frequency of the ultrasound transducer. Aliasing is prevented by increasing the pulse repetition rate of the ultrasound measurement to a sufficiently high rate, preferably above 4 kHz.

The strain rate image for the selection of the observation window can be rendered based on processing M-mode ultrasound signals by the processor according to $$\varepsilon_r = \Delta\Phi \cdot \frac{1}{\pi} \cdot \frac{f_p \cdot f_s}{2 f_c} \quad \text{(Eq. 2)}$$

with $f_s$ the data sample rate, and n the discrete time index in $\Delta\Phi = \Phi_n - \Phi_{n-1}$.

The most important properties of a tissue are the tissue contractility, the tissue elasticity and blood perfusion. The physical quantities which can reflect such properties are the tissue velocity and the strain rate. For an indication of the property of the tissue or a property change upon an external stimulus, a one-dimensional representation of tissue velocity or strain rate values as amplitude is a significant improvement with respect to a two-dimensional M-mode image, where the amplitude of the values is represented as color intensity of pixels, with brighter pixels for larger amplitudes. The human eyes are not well-fitted to detect brightness differences in two-dimensional M-mode images due to difficulty to quantitatively assess the brightness of a region of an image, and are easily misled by the brightness of a neighboring region. Furthermore, additional processing steps (e.g. filtering, downscaling) are involved for representing the ultrasound measurement signals or derived tissue velocity and strain rate values on a two-dimensional image, resulting in loss of potentially relevant information. Colors used in color maps for two-dimensional representations can raise perception differences among individuals, which is eliminated by the one-dimensional representation.

In FIG. 3 the M-mode ultrasound image 10, the tissue velocity image 20 and the strain rate image 30 are shown, originating from the same M-mode ultrasound measurement signals. The outer wall of the heart tissue in the images, corresponding to line 19, shows a stronger demarcation in the strain rate image than in the M-mode ultrasound image. The myocardium is the anatomical entity of interest in the exemplary illustration, and since its delimitation is more prominent on the strain rate image 30 than on the M-mode ultrasound image 10 or on the tissue velocity image 20, the strain rate image 30 is used in further elucidation of the invention.

Figure 4A:
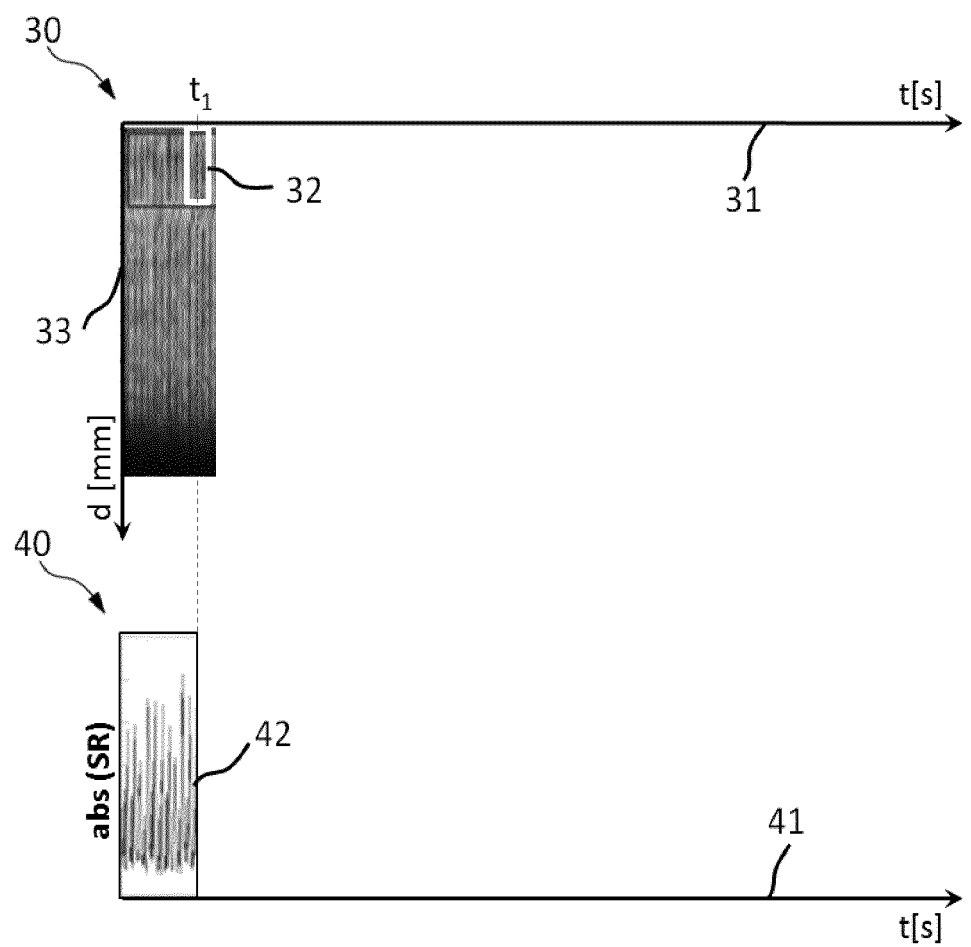
FIGS. 4a, 4b and 4c show sequences of images rendered by an embodiment of an apparatus according to the invention.

FIG. 4a shows a strain rate image 30 of a tissue at a moment $t_1$, transformed in a one-dimensional representation 40 along a temporal axis 41. The apparatus 1 for visualization of a tissue property comprises a program controlled processor and a computer program for the processor for allowing selection of the observation window 32 on the strain rate image 30. The apparatus 1 is further operable to shift the observation window 32 in the strain rate image 30 along the temporal axis 31 to enable the computation of the values 42 in the one-dimensional representation 40. The nature of the shift may be continuous or discrete. A continuous shift is the shift in time where the observation window moves a single line along the temporal axis. This is relevant for real-time processing of ultrasound signals, where the observation window can directly follow the radio frequency ultrasound signal lines as they are added real-time to the already existing portion of the M-mode ultrasound image. A discrete shift is a stepwise shift in time of the observation window with multiple lines at once. The size of the discrete steps in the preferred embodiment is smaller than the dimension of the observation window 32 along the temporal axis 31, which in practice means that the observation windows overlap along the temporal axis for consecutive computation steps in time. In the exemplary embodiment the processor is arranged to compute at any step in time a value 42 for the one-dimensional representation 40, the value 42 being defined as the mean of the absolute strain rate values in the observation window 32.

Figure 5:
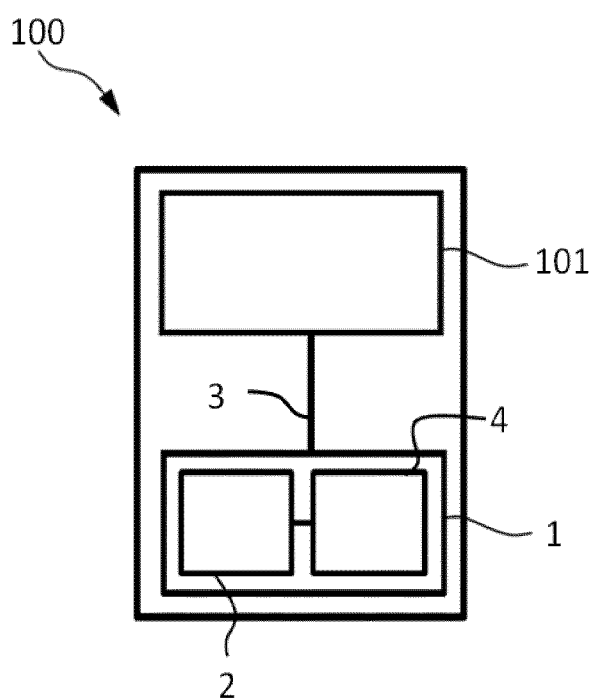
FIG. 5 shows schematically and exemplarily a measurement system comprising an ultrasound measurement arrangement and an apparatus according to the invention.

The M-mode ultrasound measurement signals can be provided to the processor 2 by an external ultrasound measurement unit through connection 3, as schematically illustrated in FIG. 1. Alternatively, the ultrasound measurement signals can be provided by a measurement system 100 exemplarily shown in FIG. 5, comprising an ultrasound measurement arrangement 101 and the apparatus 1 for visualization of a tissue property. The ultrasound measurement arrangement 101 comprises an ultrasound pulser/receiver unit connected to an ultrasound probe. The ultrasound pulser/receiver unit is arranged to send repetitively electrical pulses to the ultrasound transducer in the ultrasound probe, which transforms the electrical pulses into ultrasound waves and sends the ultrasound waves into the tissue. The ultrasound waves are scattered and reflected back from the tissue to the ultrasound transducer, which transforms the ultrasound signals into electrical signals and transmits them to the pulser/receiver unit. The pulser/receiver unit provides the ultrasound measurement signals to the signal processor 2 of the apparatus 1 through the connection 3.

Figure 6:
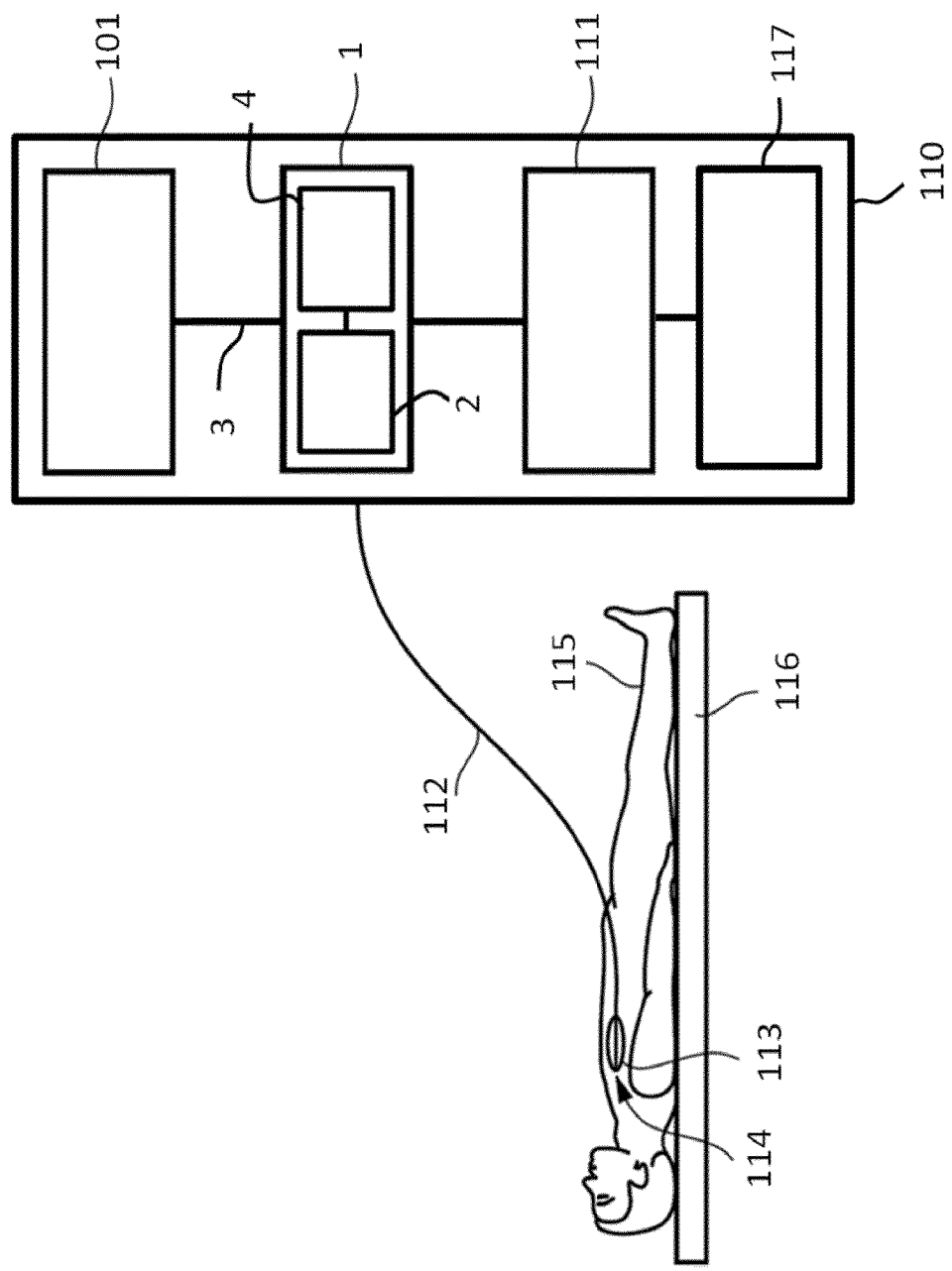
FIG. 6 shows schematically and exemplarily a system comprising an energy source connected to an energy application device, a measurement unit for measuring electrical activity, an ultrasound measurement arrangement and an apparatus according to the invention.

In yet another embodiment schematically shown in FIG. 6, the ultrasound measurement arrangement 101 can be integrated into a system for delivering energy to the tissue during ultrasound measurement. The system comprises an energy source 111 connected to an energy application device 112 for applying energy to a heart 114 tissue, the ultrasound measurement arrangement 101, a measurement unit 117 for measuring the electrical activity of the heart and the apparatus 1 for visualization of a property of the tissue. The main benefit of such a system is that the apparatus 1 can visualize not only the property of the tissue but also the property change of the tissue upon energy application to the tissue by an energy application device. The ultrasound transducers of the ultrasound measurement arrangement can be integrated into the distal tip 113 of the energy application device 112, enabling ultrasound measurement localized at the site of the energy application to the tissue. By integrating the ultrasound transducers into the energy application device, the alignment difficulties of an ultrasound probe with respect to the energy application device are eliminated, and shadowing or ringing artifacts are avoided in the ultrasound measurement. The ultrasound transducer integrated into the distal tip 113 of the energy application device 112 may be a single-piston piezoelectical transducer, a phased array piezoelectical transducer or a capacitive micro-machined ultrasound transducer (CMUT). Multiple ultrasound transducers may be integrated into the distal tip of the energy application device for providing ultrasound measurements of the heart tissue in multiple directions simultaneously or sequentially.

The ultrasound measurement from which the strain rate image 30 is derived in FIG. 4a is performed with an ultrasound transducer integrated into the distal tip 113 of the energy application device 112, wherein the distal tip 113 is in contact with the inner wall of the heart 114 tissue of a living being 115 resting on a bed 116.

The heart of a living being presents characteristic motion due to intrinsic contraction, which results in an interaction of the energy application device with the heart tissue when the energy application device is in contact with the inner wall of the heart. The intrinsic contraction is triggered by an electrical activity of the heart. The system 110, comprising a measurement unit 117 for measuring the electrical activity of the heart, can provide localized measurement of electrical activity of the heart in the vicinity of the distal tip 113 of the energy application device 112 with a sensor electrode integrated into the distal tip 113. Since the electrical activity of the heart is measured, the periodicity of the heartbeat is known. In the preferred embodiment the time interval defining the observation window 32 in the temporal direction 31 is shorter than the time interval between two consecutive heartbeats of the heart of the living being.

The cyclical variation of the interaction between the energy application device and the heart tissue is advantageous for processing statistical parameters related to tissue velocity and strain rate, since the repetitive nature of the interaction presents repetitive patterns correlated to the contraction and the relaxation phases of the heart. In case of other tissue types which do not present intrinsic motion, it is preferred that an external cyclical motion is applied on the energy application device with respect to the static tissue.

Figure 4B:
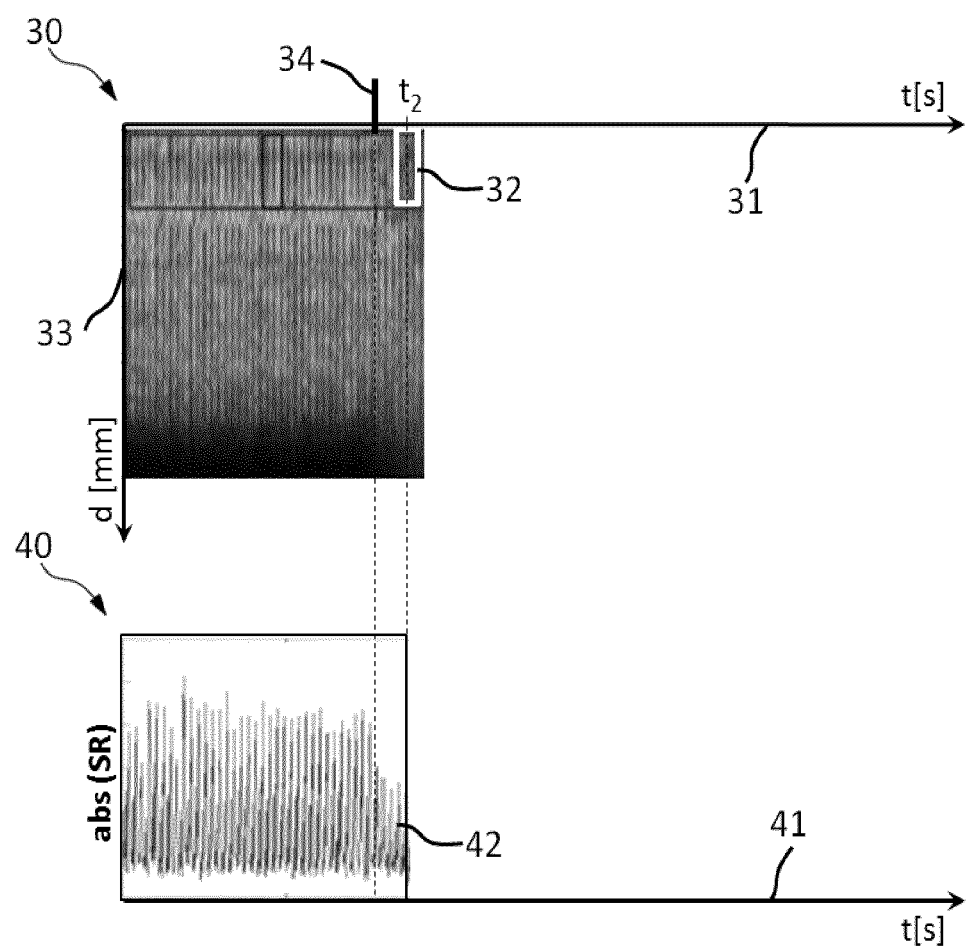

FIG. 4b shows the strain rate image 30 of the tissue at a moment $t_2$, subsequent to the inception 34 of energy application to the tissue. The energy source 111 connected to the energy application device is providing radio frequency current to the distal tip 113 of the energy application device 112. A neutral electrode (not shown) placed on the body of the living being and connected to the energy source 111 ensures that the electrical circuit is closed through the body of the living being. The radiofrequency current of 500 kHz heats the tissue locally at the contact of the heart tissue with the distal tip 113 of the energy application device, resulting in change of the values 42 in the one-dimensional representation 40. The energy source 111 in similar embodiments may provide energy to the energy application device 112 in the form of electrical current or electromagnetic radiation. In the energy application device the electrical current can be transformed in ultrasound waves, radiofrequency waves, microwaves or light. In the case of energy application to the tissue by laser radiation, the energy source can provide the energy to the energy application device directly in electromagnetic radiation through optical fiber, or it can provide electrical current which is transformed in electromagnetic radiation by a laser emitting diode integrated into the distal tip 113 of the energy application device 112.

Figure 4C:
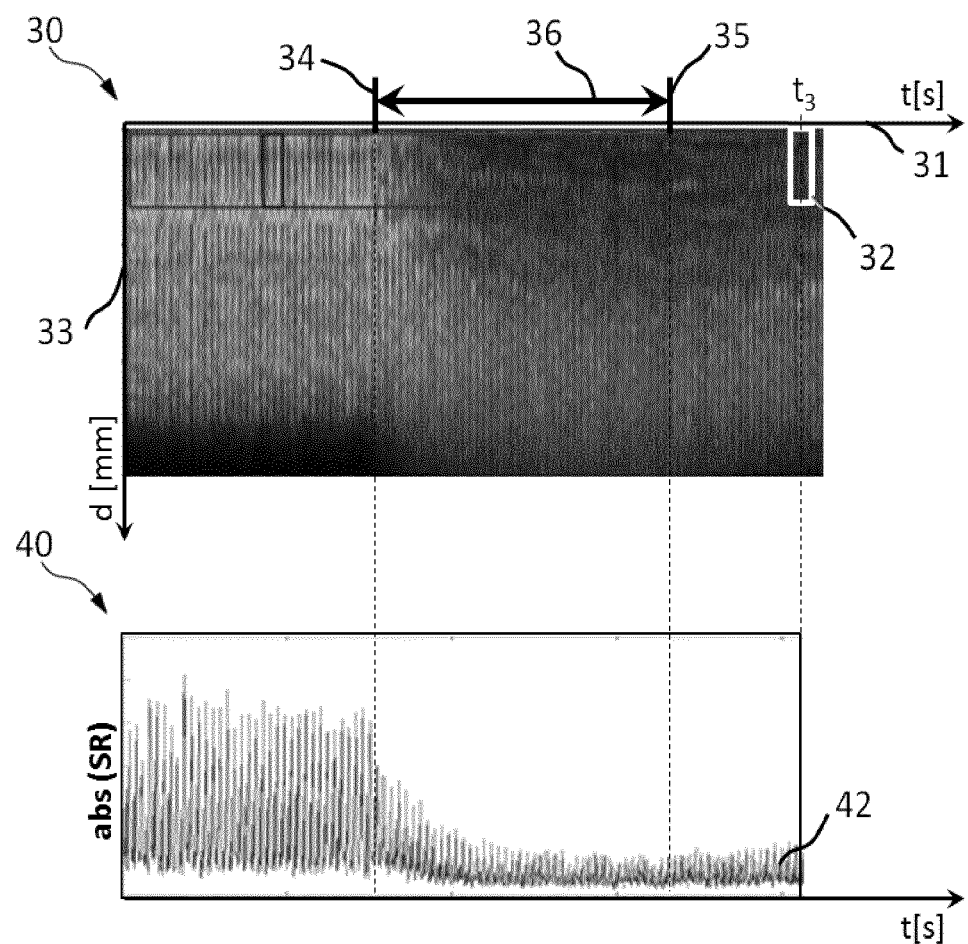

FIG. 4c shows the strain rate image 30 of the tissue at a moment $t_3$, subsequent to the termination 35 of the energy application to the tissue. During the duration 36 of energy application to the tissue, the values 42 in the one-dimensional representation 40 change in comparison to the time interval before the inception 34 of energy application, the values stabilizing within a narrow band after a certain duration of energy application.

Figure 7:
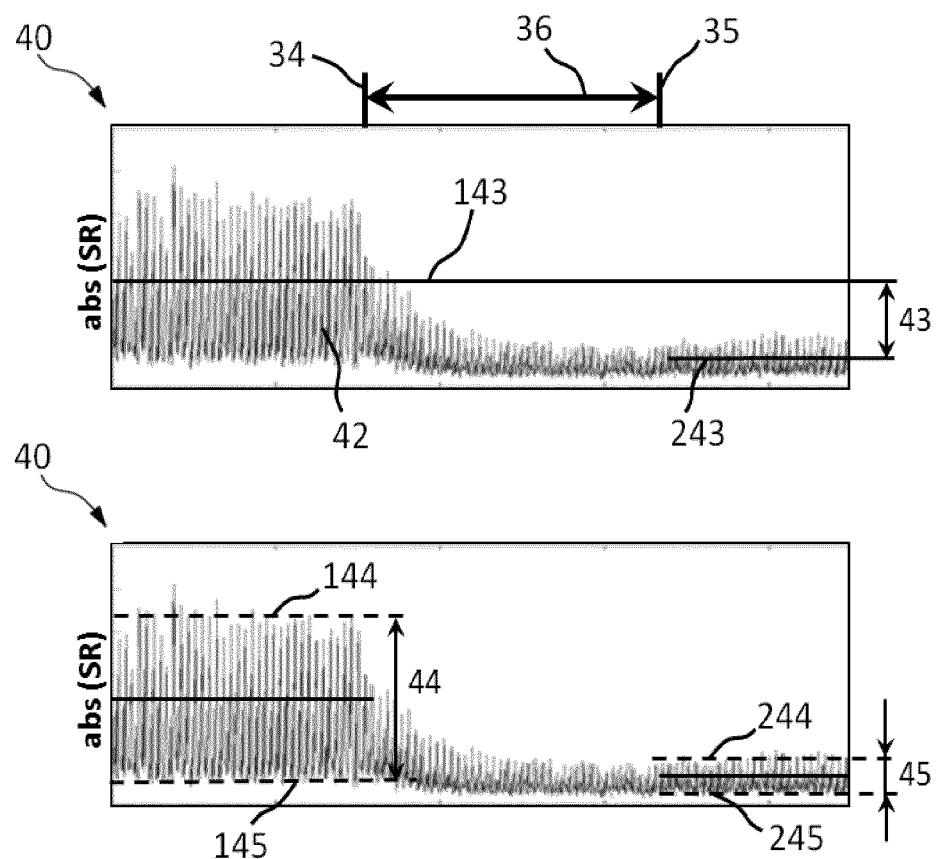
FIG. 7 shows schematically and exemplarily the differences in the one-dimensional representation of strain rate values, characteristic to a property change of a tissue upon application of energy.

The characteristics of the one-dimensional representation 40 are further elucidated in FIG. 7. The periodical variation of the values 42 is caused by the cyclical interaction of the distal tip 113 of the energy application device with the heart 114 tissue during heart motion and breathing of the living being. Before the inception 34 of energy application to the tissue, the values 42 in the representation 40 are characterized by a mean 143 and a variation 44. The minimum 145 and the maximum 144 of the values define the variation 44. During energy application 36 to the tissue, the values 42 in the one-dimensional representation change until they stabilize in a narrow and consistent band 45 defined by the minimum 245 and maximum 244 of the values, with a mean 243. The stabilization of the values 42 in the narrow band is an indication of completion of the property change of the tissue throughout the entire spatial dimension y defining the observation window 32. An offset 43 characterizes the difference between the mean 143 before energy application to the tissue and the mean 243 after termination of energy application to the tissue.

The offset between the means and the variation of the values are dependent on the conditions of the tissue interaction with the energy application device. The interaction is influenced by the mechanical restraint of the heart tissue by the distal tip of the energy application device, by the variation of the tissue contractility with the anatomical location in the heart, and additionally by the motion of adjacent organs such as lungs during breathing of the living beings. Tracking technologies based on ultrasound, radiology, electromagnetism or magnetic resonance, are able to provide information on the position of the energy application device in the heart and on the circumstances of the interaction between the energy application device and the heart tissue.

In the atria of a living being a change of the mean 143 and a change of the variation 44 of the values in the range of 10 to 30 percent is indicative that the tissue property change is completed upon energy application to the tissue throughout the entire spatial dimension y defining the observation window 32, provided that the offset between the means 43 and the variation 45 of the values are constant for a certain time interval.

The strain rate image 30 used for selection of the observation window is positioned preferentially above the one-dimensional representation 40, however the two representations may be positioned side by side.

Figure 8:
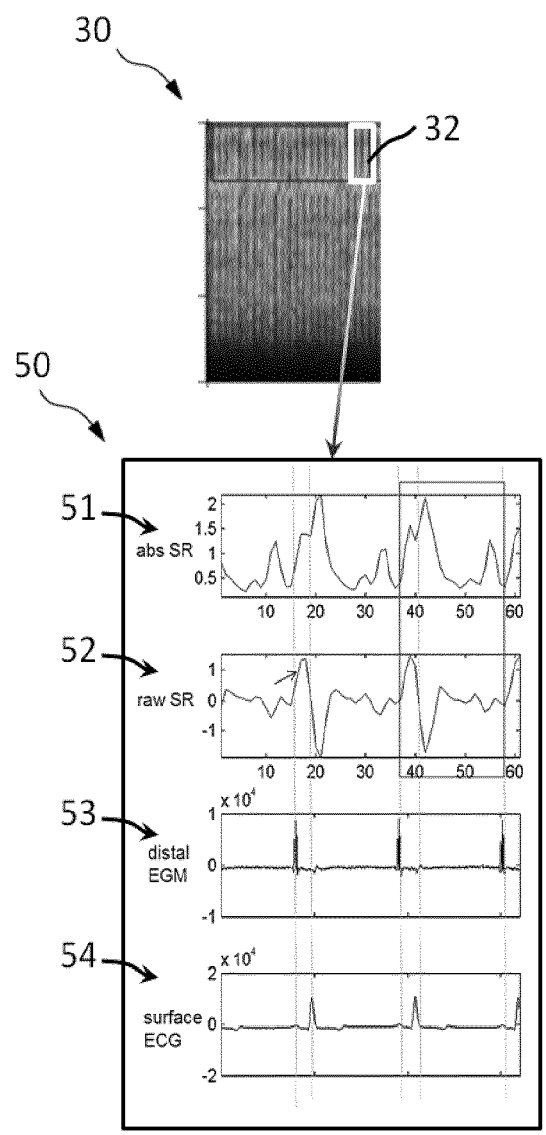
FIG. 8 shows schematically and exemplarily an image of combined one-dimensional representations of strain rate values and synchronized electrograms.

FIG. 8 shows schematically and exemplarily an image 50 comprising four one-dimensional representations 51,52,53, 54. The upper two one-dimensional representations 51 and 52 are representing the mean of the absolute strain rate values and the mean of the strain rate values respectively, computed in the observation window 32 of the tissue strain rate image 30. The lower two one-dimensional representations 53 and 54 are representing two signals of the electrical activity of a heart, respectively a distal electrogram and a surface electrocardiogram. The system 110 comprises a measurement unit 117 for measuring electrograms and/or electrocardiograms. Electrograms are electrical signals measured locally in a vicinity of the heart 114 tissue with sensor electrodes (e.g platinum-iridium alloy) integrated into the distal tip 113 of the energy application device 112. Electrocardiograms are electrical signals measured with electrodes positioned and fixed onto the surface of the body of the living being 115. Both, electrograms and electrocardiograms are synchronized with the ultrasound measurement signals.

Figure 9:
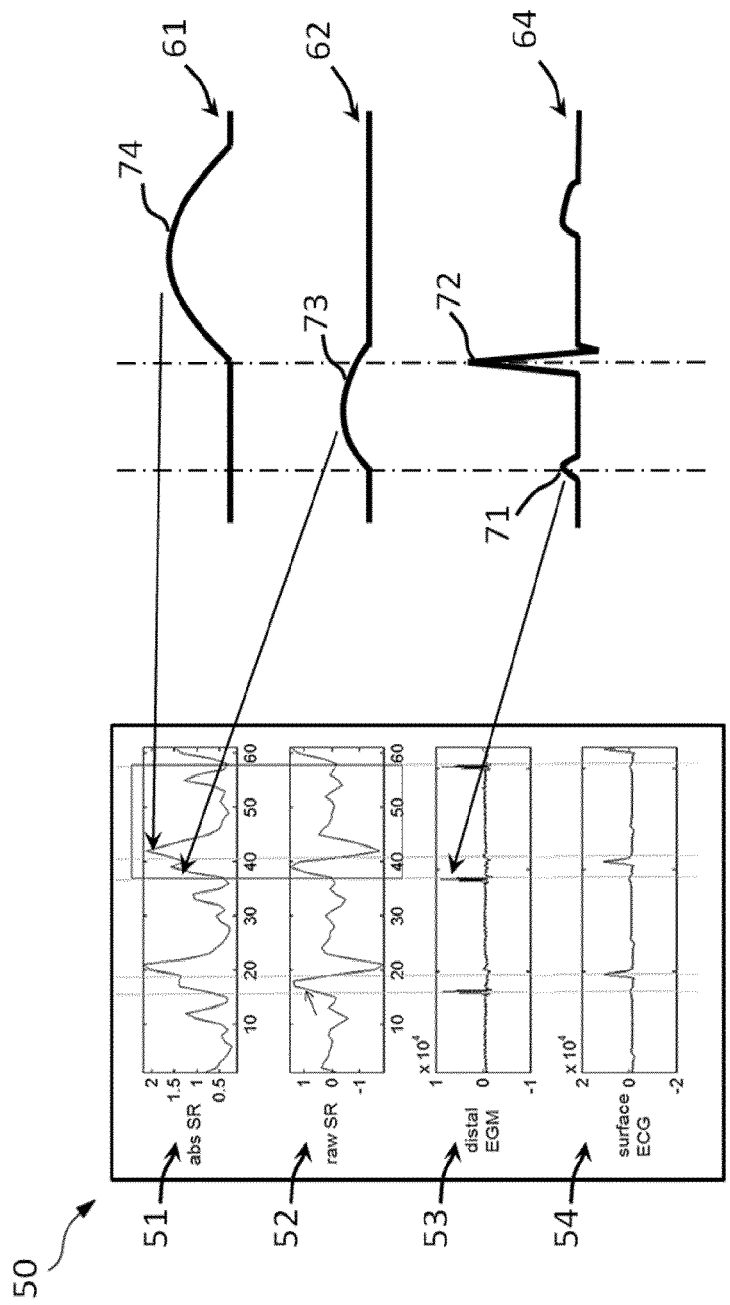
FIG. 9 shows schematically and exemplarily the relationship between the electrical activity of a heart and the mechanical interaction between an energy application device with the heart tissue.

FIG. 9 shows schematically and exemplarily the relationship between the one-dimensional representations 51,52 and the synchronized one-dimensional representations of the electrical activity of the heart 53,54. The one-dimensional representation 51 can be regarded as being the one-dimensional representation 40 from FIG. 4a with magnified time scale. A schematic signal representing an electrocardiogram for one heartbeat cycle of a living being is shown with 64, which is corresponding to the one-dimensional representation of the electrocardiogram 54 for the observation window 32 in the respective time interval. The electrocardiogram 64 comprises the electrical activation signal of the atria 71 and the electrical activation signal of the ventricles 72. The electrical activation signal of the atria 71 initiates the atrial contraction 73 according to the schematic mechanical behavior diagram of the atria 62, whereas the electrical activation signal of the ventricles 72 initiates the contraction of the ventricles 74 according to the schematic mechanical behavior diagram of the ventricles 61. In the exemplary description, the distal tip 113 of the energy application device 112, comprising the ultrasound transducer for pulse/echo measurement and the sensor electrode for measurement of the electrical activation signal of the heart, is positioned in the atrium of the heart, in contact with the inner wall of the heart. Therefore, the electrogram 53 measured with the sensor electrode integrated into the distal tip 113 of the energy application device 112 is primarily sensing the atrial activation 71 corresponding to the elevated peaks in the one-dimensional representation 53, whereas only small electrical disturbance is sensed by the same sensor electrode as far field signal during electrical activation of the ventricles.

The atrial and ventricular contractions 73 and 74 triggered by the electrical activation signals 71 and 72 respectively, cause a mechanical interaction of the distal tip of the energy application device with the heart tissue upon contact. The atrial and ventricular contractions 73 and 74 are recognizable as prominent peaks in the representations 51 and 52. Although the distal tip of the energy application device is in contact only with the inner wall of the atrium, the strong ventricular contraction causes a significant mechanical interaction between the atrial tissue and the distal tip of the energy application device. In the exemplary description, the mechanical interaction of the distal tip of the energy application device is resulting in larger strain rate values during ventricular contraction than during the atrial contraction. This can be observed in the representation 51, though from the representation 52 it can be concluded that the signs of the strain rate values are reversed during the interactions attributed to atrial and ventricular contractions.

Since the ultrasound measurement is synchronized with the measurement of the electrical activation signals of the heart, and the mechanical behavior of the heart triggered by the electrical activity is generating the interaction of the energy application device with the heart tissue, the representation of the mechanical interaction in the one-dimensional representations 51 and 52 can be considered mechanograms in analogy to the electrogram of the heart.

Figure 10:
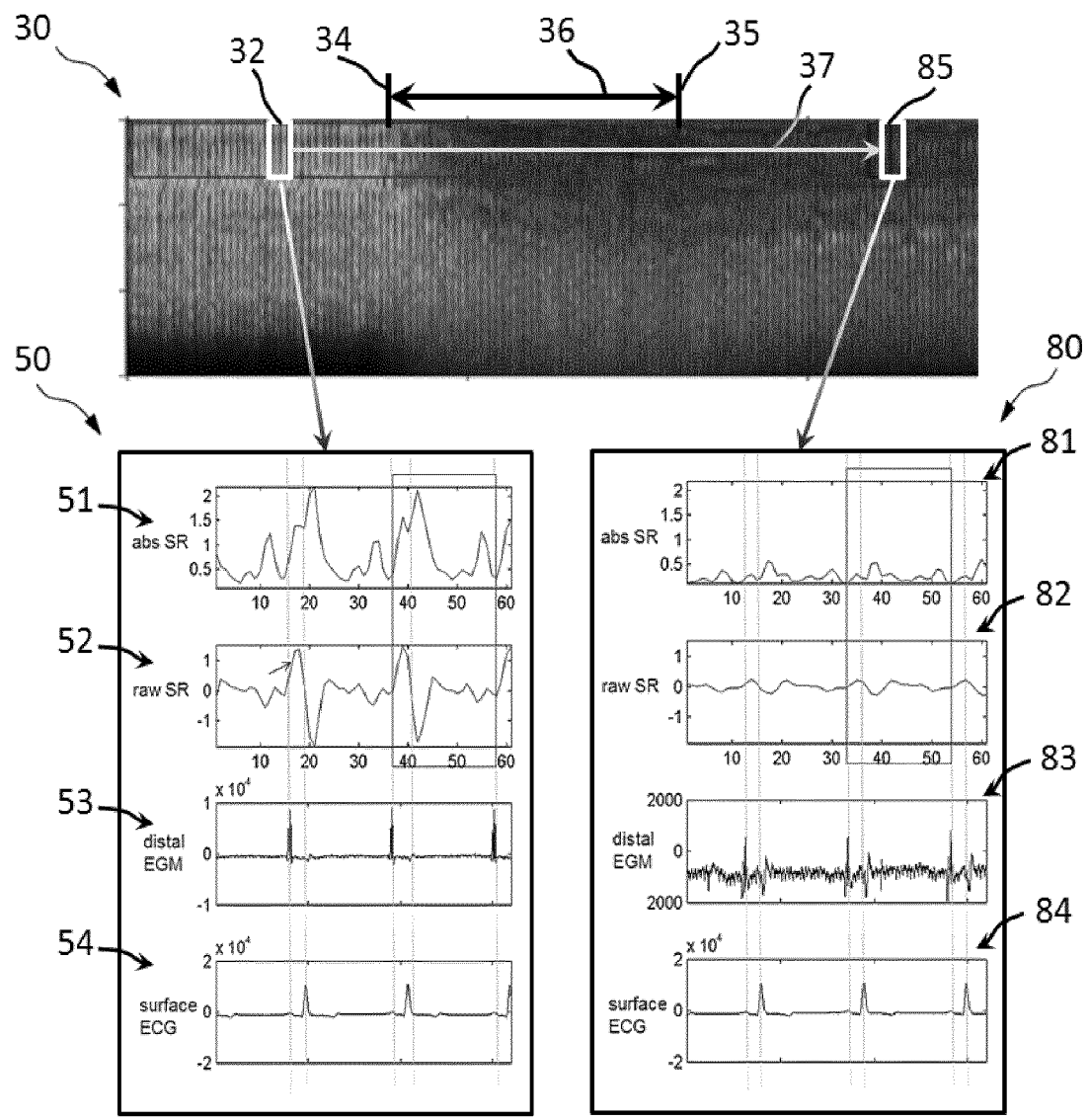
FIG. 10 shows schematically and exemplarily one-dimensional representations of strain rate values synchronized with electrograms, before and after energy application.

In FIG. 10 the image 50 of the combined four representations 51,52,53,54 is shown at an instance before the inception 34 of energy application to the heart tissue and at an instance after discontinuation 35 of energy application to the tissue. The image 80 of the combined representations 81,82,83,84 has the same significance and represents the same entities as in image 50, only at a different instance. The observation window 85 is the same observation window as 32, only shifted 37 along the temporal axis beyond the termination 35 of energy application to the tissue. The electrocardiogram measured on the surface of the body of the living being remains identical in both cases 54 and 84. This is an indication that due to energy application very locally to the heart tissue with the distal tip of the energy application device, on an overall ensemble the electrical activity of the heart has not changed. However, the atrial electrical activation signal, measured locally with the sensor electrode integrated into the distal tip, is strongly diminished, which is an indication that the energy application has changed the electrical property of the inner wall of the heart tissue locally, where the distal tip is in contact with tissue. The upper two one-dimensional representations at the two different instances 51,52 and 81,82 respectively, show a strong reduction of the strain rate values after termination 35 of energy application to the tissue, which is indicative of the change in mechanical interaction between the heart tissue and the distal tip of the energy application device.

The main advantage of using the combined image 50 of the one-dimensional representations 51,52,53,54 is the possibility to distinguish between temporary effect (e.g. tissue stunning) and permanent effect of the energy application on the electrical activity of the heart. The temporary effect is not translating into significant influence on the mechanical interaction between the heart tissue and the distal tip of the energy application device despite a change on the electrogram, whereas the permanent effect does result in significant diminution of the mechanical interaction between the distal tip of the energy application device and the heart tissue, as shown in the one-dimensional representations 81,82. Furthermore, the mechanical interaction from 51,52 can be associated to specific electrical activity sequences of various anatomical structures of the heart 53,54.

The combined image 50 may contain alternatively other one-dimensional representations related to tissue velocity. The preferred embodiment of the combined image 50 is a one-dimensional representation of strain rate values 51, an electrogram 53 measured with the sensor electrode integrated into the distal tip of the energy application device and an electrocardiogram 54 measured on the surface of the body of the living being.

Figure 11:
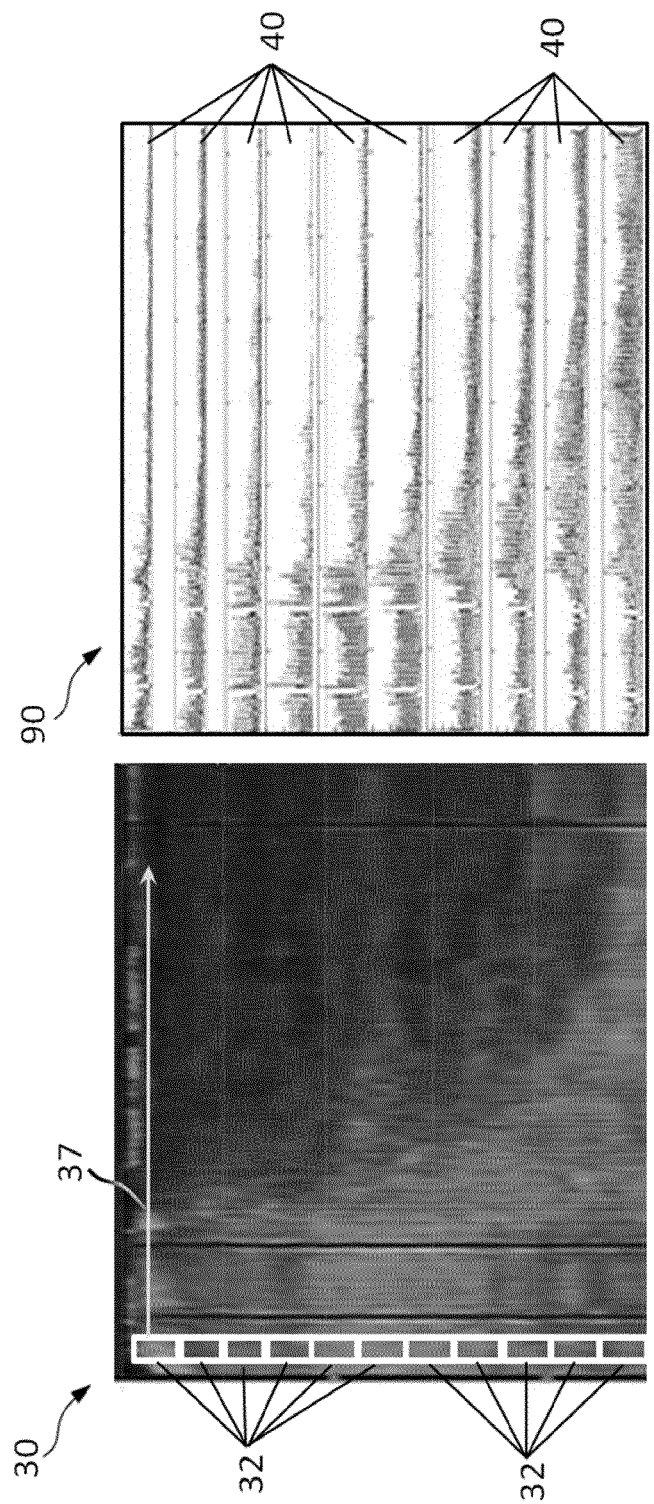
FIG. 11 shows a composite image consisting of multiple one-dimensional representations of strain rate values, originating from a plurality of observation windows.

FIG. 11 shows schematically and exemplarily an embodiment wherein the rendering device coupled to the processor is operable to render a composite image 90 consisting of the plurality of one-dimensional representations along the temporal axis, wherein the position of each one-dimensional representation in the composite image 90 is according to the subsequent position of the observation windows 32 in the strain rate image 30, motion-mode ultrasound image or tissue velocity image from which they originate. In the strain rate image 30, the spatial direction is divided into multiple adjacent observation windows 32. The size of the observation windows in spatial and temporal directions is defined with a computer program for the processor and a program controlled processor. One-dimensional representation 40 along the temporal axis is rendered for each of the observation windows upon processing the ultrasound measurement signals into strain rate values by shifting 37 the observation windows 32 along the temporal axis. The plurality of one-dimensional representations 40 are positioned in the spatial direction of the composite image 90 according to the subsequent position of the observation windows 32 in the strain rate image 30 from which they originate. The composite image 90 can be displayed side by side with the strain rate image 30, or alternatively below the strain rate image. Instead of the strain rate image an ultrasound M-mode image or a tissue velocity image may be used for definition of the size of the observation windows. The observation windows in the spatial direction may overlap for improved refinement of the composite image. The preferred overlap between the observation windows is 50 percent. The composite image 90 may allow magnification of the time scale for the one-dimensional strain rate representations, similar to FIG. 8. In that case, the resulting composite image is augmented with one-dimensional representations of the electrical activity of the heart in the form of an electrogram 53 and/or an electrocardiogram 54.

The composite image 90 consisting of the plurality of one-dimensional representations improves the presentation of the tissue property change upon application of energy such that the propagation of the change in the values of the subsequent one-dimensional representations is reflecting the progression of a property change along the spatial dimension.

Figure 12:
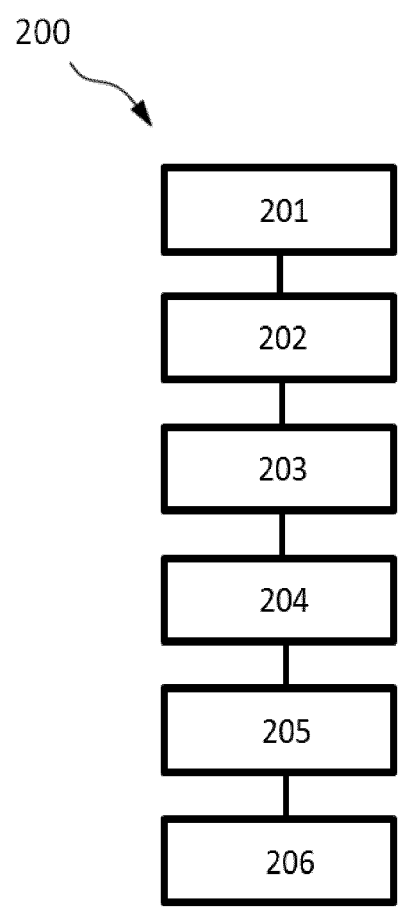
FIG. 12 shows a schematic diagram for discontinuation of energy application to the tissue by the system.

FIG. 12 shows schematically and exemplarily a diagram 200 of the functional use of the system 110. Ultrasound measurement starts in step 201, which can serve initially for positioning the distal tip 113 of the energy application device 112 with respect to the heart 114 tissue and then for ultrasound measurement on the tissue. The system starts measuring and recording the electrical activity of the heart with the measurement unit 117 connected to sensor electrodes integrated into the distal tip of the energy application device and through the electrodes positioned and fixed on the surface of the body of the living being.

In step 202 the signal processor 2 is arranged to process ultrasound measurement signals transferred via connection 3 from the ultrasound measurement arrangement 101. A program controlled processor and a computer program for the processor enables the selection of the observation window 32 based on an M-mode ultrasound image or alternatively on a tissue velocity image or a strain rate image either by using a pointing device or by indicating the size, coordinate position and the shape of the observation window.

In step 203 the one-dimensional representation 40 is rendered by the rendering device 4 coupled to the processor, representing values of statistical parameters of the tissue velocity or the strain rate. Alternatively, when magnification of the time scale for the one-dimensional representation 40 is selected, than the one-dimensional representation of the electrical activity 53,54 of the heart is rendered together with the one-dimensional representation of the mechanical interaction of the energy application device with the heart tissue, forming a combined image 50.

In step 204 the energy application to the tissue starts. The energy is delivered to the tissue through a distal tip 113 of the energy application device 112 connected to the energy source 111 of the system 110. During application of energy 36 to the tissue, the offset of the means 43 and the variation 44 of the values 42 gradually change, meaning that the property of the tissue in the observation window 32 is changing progressively.

In step 205 the processor detects that the offset of the means 43 and the variation 45 of the values become constant for a certain time interval. When that occurs, the change of the tissue property upon energy application is completed throughout the entire spatial dimension y defining the observation window 32, and the energy application can be terminated, provided that the change of the mean 143 and the change of the variation 44 of the values exceed a predetermined threshold. In the atria of a living being the threshold is in the range of 10 to 30 percent.

Alternatively, the threshold can be regarded as endpoint for the termination of energy application to the tissue and it can be defined with a program controlled processor and a computer program for the processor.

When the conditions in step 205 are fulfilled, the processor is arranged to send a signal to the energy source 111, and in step 206 the energy source discontinues transmission of energy to the energy application device upon receiving the signal. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the internet or other wired or wireless telecommunication systems.

Any reference signs in the claims should not be construed as limiting the scope.

The invention claimed is:

1. A system comprising:
at least one processor configured for communication with:
an ultrasound transducer configured to obtain ultrasonic image data representing the tissue; and
a display,
wherein the at least one processor is configured to:
obtain the ultrasonic image data from the ultrasound transducer, wherein a first dimension of the ultrasonic image data comprises a spatial dimension and a second dimension of the ultrasonic image data comprises a time dimension;
determine, based on the ultrasonic image data, a first plurality of strain rate values and a second plurality of strain rate values, wherein each strain rate value of the first plurality of strain rate values and the second plurality of strain rate values represents a spatial region of the tissue along the spatial dimension and a period of time along the time dimension, wherein the spatial region for the first plurality of strain rate values is different than the spatial region for the second plurality of strain rate values, wherein the period of time for each strain rate value of the first plurality of strain rate values is different from one another, and wherein the period of time for each strain rate value of the second plurality of strain rate values is different from one another;
generate a graphical representation of the first plurality of strain rate values and the second plurality of strain rate values;
provide the graphical representation for presentation on the display,
wherein the spatial region along the spatial dimension and the period of time along the time dimension define an observation window in the ultrasonic image data, and
wherein, to determine the second plurality of strain rate values, the processor is configured to shift the observation window along the spatial dimension from a first position corresponding the spatial region for the first plurality of strain rate values to a second position corresponding to the spatial region for the second plurality of strain rate values.

2. The system of claim 1,
wherein the at least one processor is configured for communication with:
an energy source connected to an energy application device for applying energy to a tissue so as to change a property of the tissue; and
wherein the at least one processor is configured to:
determine a change associated with at least one of the first plurality of strain rate values or the second plurality of strain rate values; and
cause the energy source to discontinue transmission of the energy to the energy application device in response to the determination of the change.

3. The system according to claim 2, wherein the at least one processor is configured to:
process the ultrasonic image data to form processed ultrasonic image data; and
generate the graphical representation of the first plurality of strain rate values and the second plurality of strain rate values based on the processed ultrasonic image data.

4. The system according to claim 3, wherein the at least one processor is configured to visualize a motion of a heart of a living being.

5. The system according to claim 4, wherein the period of time is shorter than a time interval between two consecutive heartbeats of the heart of the living being.

6. The system according to claim 4, wherein the at least one processor is further configured for communication with a measurement unit for measuring an electrical activity of the heart.

7. The system according to claim 6, wherein the at least one processor is configured to synchronize the graphical representation of the first plurality of strain rate values and the second plurality of strain rate values with an electrogram or an electrocardiogram representing the electrical activity of the heart.

8. The system according to claim 7, wherein the at least one processor is configured to generate the graphical representation of the first plurality of strain rate values and the second plurality of strain rate values together with a graphical representation of the electrogram and/or the electrocardiogram of the heart in a combined image.

9. The system according to claim 2, wherein at least one of the period of time associated with each strain rate value of the first plurality of strain rate values partially overlap along the time dimension or the period of time associated with each strain rate value of the second plurality of strain rate values partially overlap along the time dimension.

10. The system according to claim 2, wherein the energy application device is arranged to apply the energy to the tissue by a modality selected from ultrasound waves, radiofrequency current, radiofrequency waves, microwaves, or laser radiation.

11. The system according to claim 2, wherein the discontinuation of the transmission of the energy to the energy application device is in response to a detected change in the range of 10 to 30 percent.

12. The system according to claim 2, wherein the ultrasound transducer is integrated into a distal tip of the energy application device.

13. The system according to claim 12, wherein an electrical signal measurement electrode is integrated into the distal tip of the energy application device.

14. The system according to claim 2,
wherein the at least one processor is configured to determine, a change in a mean and a variation of at least one of the first plurality of strain rate values or the second plurality of strain rate values, and wherein the change associated with at least one of the first plurality of strain rate values or the second plurality of strain rate values comprises a change in the mean and the variation of at least one of the first plurality of strain rate values or the second plurality of strain rate values.

15. The system of claim 1,
wherein the spatial region for the first plurality of strain rate values is the same as one another, and
wherein the spatial region for the second plurality of strain rate values is the same as one another.

16. The system of claim 1,
wherein, to determine the second plurality of strain rate values, the processor is configured to:
shift the observation window to a plurality of positions along the time dimension such that the period of time for each strain rate value of the second plurality of strain rate values is different.

17. The system of claim 1, wherein the first position of the observation window along the spatial dimension and the second position of the observation window along the spatial dimension overlap along the spatial dimension.

18. The system according to claim 1,
wherein, to determine the first plurality of strain rate values, the processor is configured to shift the observation window to a plurality of positions along the time dimension such that the period of time for each strain rate value of the first plurality of strain rate values is different, and
wherein the first plurality of strain rate values respectively correspond to the plurality of positions of the observation window.

19. The system according to claim 18, wherein the plurality of positions of the observation window overlap along the time dimension.

* * * * *